US00PP31868P3

(12) United States Plant Patent
Couturieux

(10) Patent No.: US PP31,868 P3
(45) Date of Patent: Jun. 16, 2020

(54) ***SORBARIA* PLANT NAMED 'COUSORB05'**

(50) Latin Name: *Sorbaria sorbifolia*
Varietal Denomination: COUSORB05

(71) Applicant: Jacques Couturieux, Moyenmoutier (FR)

(72) Inventor: Jacques Couturieux, Moyenmoutier (FR)

( * ) Notice: Subject to any disclaimer, the term of this patent is extended or adjusted under 35 U.S.C. 154(b) by 0 days.

(21) Appl. No.: 16/350,496

(22) Filed: Nov. 19, 2018

(65) Prior Publication Data

US 2019/0230834 P1 Jul. 25, 2019

(30) Foreign Application Priority Data

Jan. 19, 2018 (QZ) ..... PBR 2018/00115

(51) Int. Cl.
*A01H 5/02* (2018.01)
*A01H 6/74* (2018.01)

(52) U.S. Cl.
USPC ..... Plt./226
CPC ..... *A01H 6/74* (2018.05)

(58) Field of Classification Search
USPC ..... Plt./226
CPC ..... A01H 5/00; A01H 5/02
See application file for complete search history.

(56) References Cited

PUBLICATIONS https://www.floraldaily.com/article/9011274/novelties-at-plantarium-2017/; Aug. 11, 2017; 25 pages.*

* cited by examiner

*Primary Examiner* — Kent L Bell
(74) *Attorney, Agent, or Firm* — Cassandra Bright

(57) ABSTRACT

A new and distinct *Sorbaria* cultivar named 'COUSORB05' is disclosed, characterized by a compact plant size having early budding and easy care in the garden. Plants have an attractive young foliage color of pink and yellow-green for an extended period. The new variety is a *Sorbaria sorbifolia* for use as a commercial rootstock for grafting or budding onto.

4 Drawing Sheets

Latin name of the genus and species: *Sorbaria sorbifolia*. Variety denomination: 'COUSORB05'.

BACKGROUND OF THE INVENTION

The new cultivar is a product of a breeding scheme conducted by the inventor Jacques Couturieux. The new variety was discovered in Vosges, France, as an individual seedling of the patented variety *Sorbaria sorbifolia* 'Sem', U.S. Plant Pat. No. 16,336. The new variety rose as a seedling resulting from the self-pollination of the parent variety. This plant with unique characteristics was selected during April of 2014.

Asexual reproduction of the new cultivar 'COUSORB05' was first performed via semi-softwood tip cuttings in Vosges, France, during June of 2014. Subsequent propagation has shown that the unique features of this cultivar are stable and reproduced true to type on successive generations.

SUMMARY OF THE INVENTION

The cultivar 'COUSORB05' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'COUSORB05'. These characteristics in combination distinguish 'COUSORB05' as a new and distinct *Sorbaria* cultivar:

1. Compact size.
2. Early budding.
3. Young leaf coloration of pink and yellow-green for an extended period.
4. Cold-resistant.
5. Easy care in the garden, with no maintenance needed.

PARENT COMPARISON

Plants of the new cultivar 'COUSORB05' are similar to plants of the parent, in most horticultural characteristics. Plants of the new cultivar 'COUSORB05', however, differ in the following:

1. Plants of the new cultivar are more compact than the parent variety.
2. New variety's young leaf coloration lasts longer than parent variety.

COMMERCIAL COMPARISON

Plants of the new cultivar 'COUSORB05' can also be compared to the unnamed, unpatented *Sorbaria sorbifolia* sold in the nursery trade. Plants are similar in most horticultural characteristics, however, plants of the new cultivar 'COUSORB05' differ in the following:

1. Plants of the new variety are more compact.
2. Plants of the new variety have yellow-green and pink new foliage coloration not seen in this comparator.

BRIEF DESCRIPTION OF THE PHOTOGRAPHS

The accompanying photographs illustrate in full color typical plants of 'COUSORB05' in Moyenmoutier, France. The photographs were taken using conventional techniques and equipment. While the colors in these photographs may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of the new *Sorbaria* plant. No artificial light, photoperiodic treatments or chemical treatments were given to the plants.

DETAILED BOTANICAL DESCRIPTION

Figure 1:
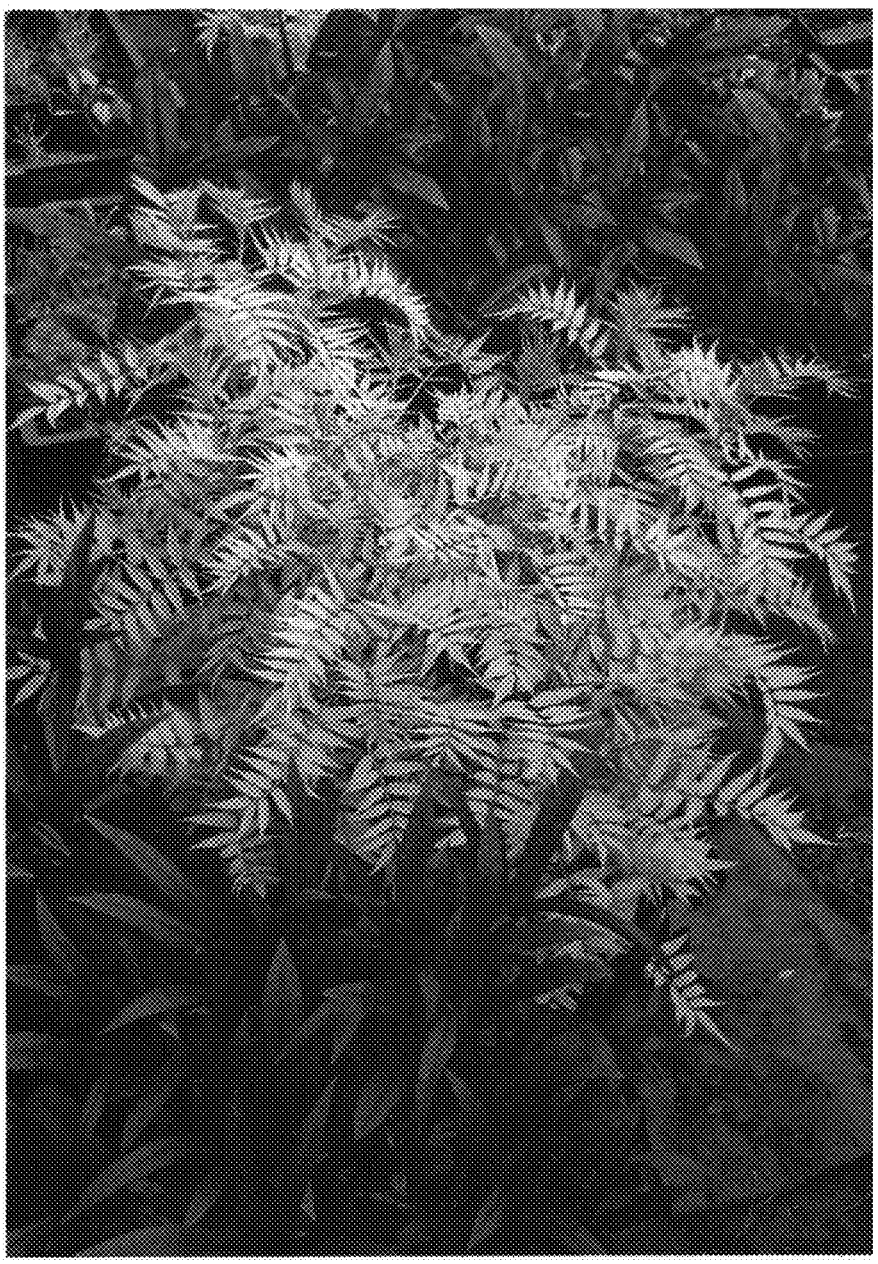
FIG. 1 illustrates in full color a young 'COUSORB05' in the month of April.
Figure 2:
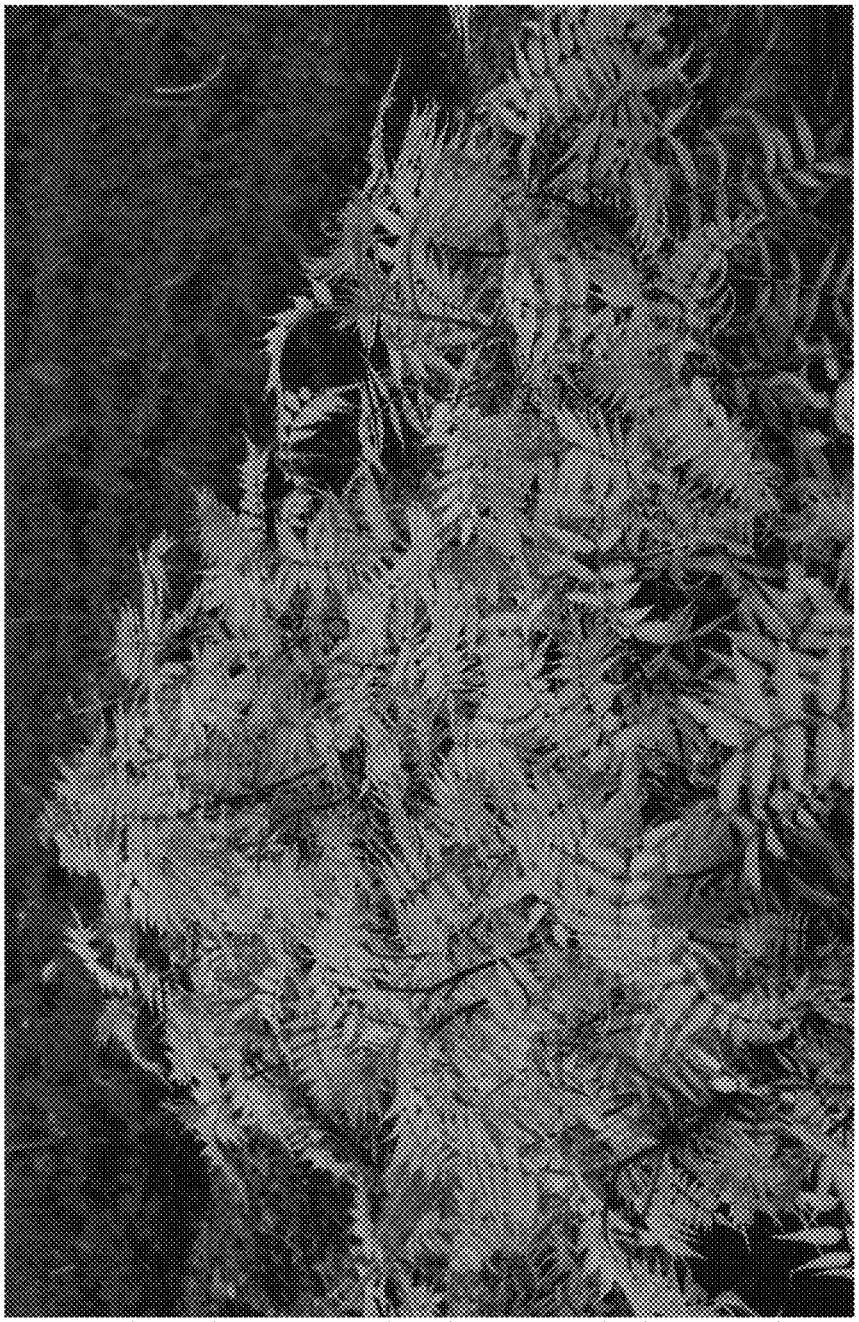
FIG. 2 illustrates in full color 'COUSORB05' foliage in May.
Figure 3:
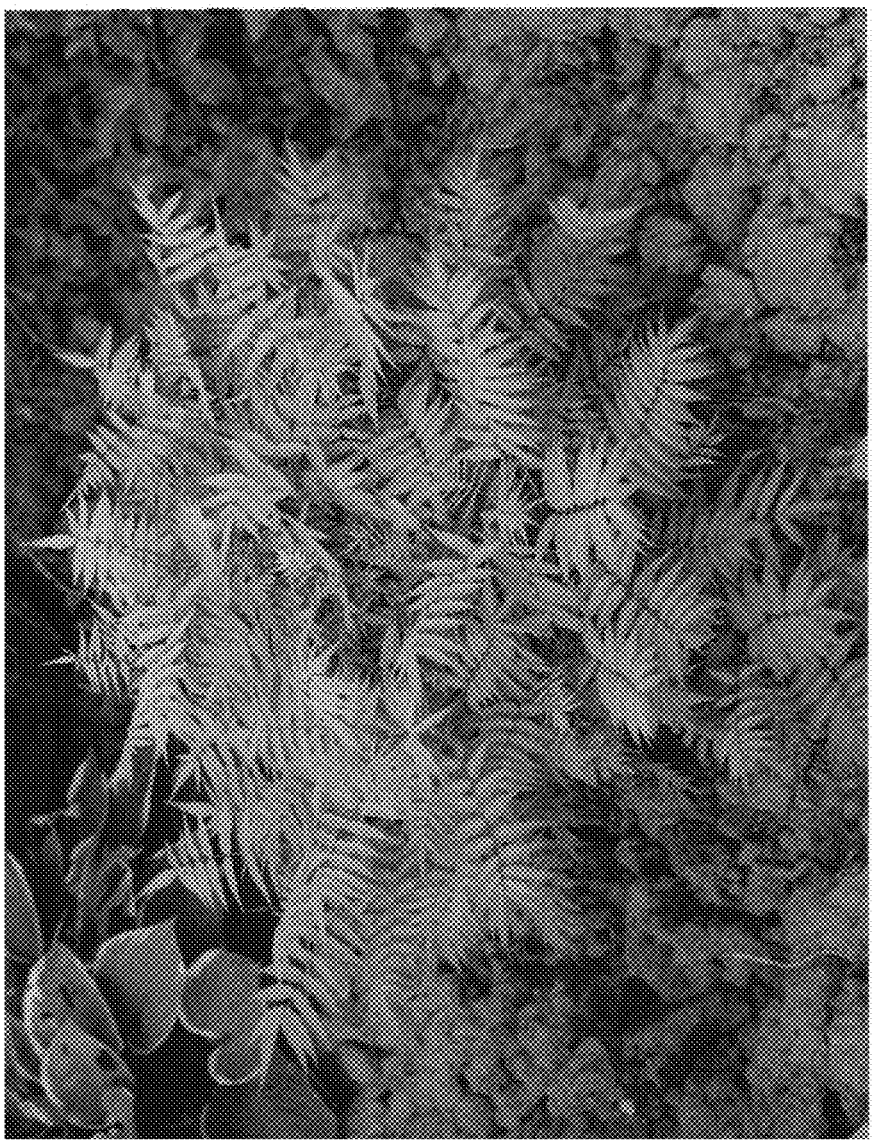
FIG. 3 illustrates in full color 'COUSORB05' foliage in June.
Figure 4:
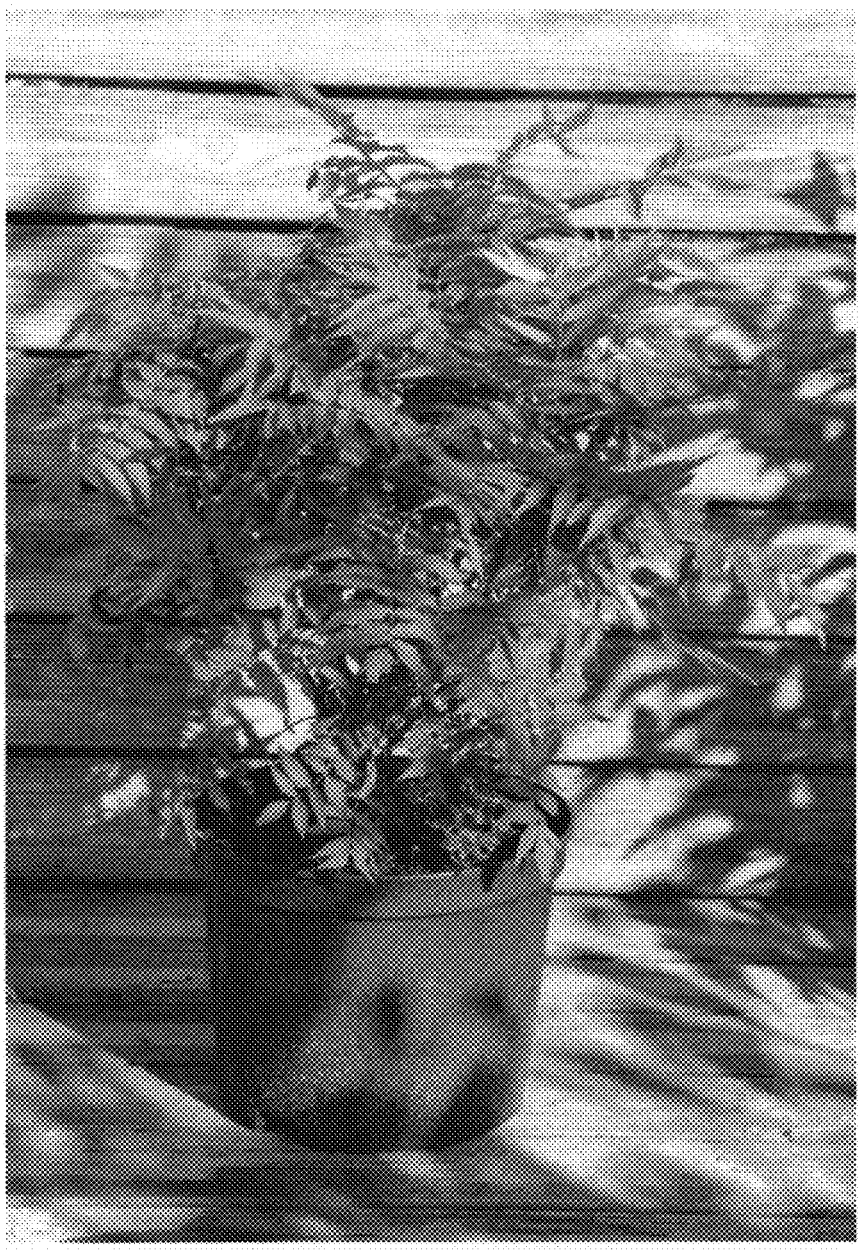
FIG. 4 illustrates in full color a mature 'COUSORB05' in the month of September.

In the following description, color references are made to The Royal Horticultural Society Colour Chart 2007 except where general terms of ordinary dictionary significance are used. The following observations and measurements describe 'COUSORB05' plants grown outdoors in Vosges, France. Measurements were taken from plants of approximately 2 years of age. Measurements and numerical values represent averages of typical plant types at corresponding states of maturity.

Botanical classification: *Sorbaria sorbifolia* 'COUSORB05'.

Propagation:

*Time to initiate roots.*—About 21 days at approximately 27° C.

*Root description (color, woody, fibrous, branching characteristics).*—Roots are fibrous and somewhat branched. Newly formed roots are delicate and fleshy, 1 to 2 mm in diameter. Mature roots are woody and more rigid.

*Propagation method.*—Softwood cuttings.

Plant:

*Height.*—150 cm.

*Plant spread.*—About 100 cm.

*Plant habit.*—Upright globular.

*Growth rate.*—Moderate to rapid.

*Growth habit.*—Upright, compact deciduous shrub.

*Branching characteristics.*—Free branching, 4 to 8 main branches, suckers and lateral produced.

*Branch length.*—Average range 20 to 45 cm.

*Branch diameter.*—0.6 to 1.4 cm.

*Branch texture.*—Glabrous.

*Branch color.*—Near RHS Grey-Brown 199C.

*Internode length.*—2 to 6 cm.

*Age of plant described.*—About 2 years.

Foliage:

*Leaf.*—Arrangement: Alternate occurring compound leaves. Length: Average range 20 to 25 cm. Width: Average 7 cm. Leaflets: Shape: Lanceolate. Quantity: 11 to 17. Occurring in opposite pairs, with or without a single terminal leaflet. Length: Average range 5 to 7 cm. Width: Average 2.5 cm. Attachment: Sessile. Apex: Acuminate. Base: Rounded. Margin: Dentate, crenate. Color: Young foliage first emerging upper side: Near RHS Red 43C, then fading to Red 43D and Red 38D. Young foliage under side: Near RHS Red 43C, then fading to Red 43D and Red 38D. Spring semi-mature foliage upper side: Near RHS Red 38B, 38C and 38D. Turning Yellow-Green 150C. Spring semi-mature foliage under side: Near RHS Red 38B, 38C and 38D. Turning Yellow-Green 150C. Summer mature foliage upper side: Near RHS Green 136B. Summer mature foliage under side: Near RHS Green 136B. Venation: Type: Pinnate. Venation color: Upper Surface: Immature near Red 45D, mature near Yellow-Green 150B. Lower Surface: Immature near Red 45D, mature near Yellow-Green 150B.

*Petiole.*—

*Length.*—About 2 to 5 cm.

*Diameter.*—About 5 mm.

*Color.*—Immature near Red 45D, mature near Yellow-Green 150B.

*Texture.*—Glabrous.

Flower: Flowering not observed to date.

Reproductive organs: Not observed to date.

Other characteristics:

*Seeds and fruits.*—Not observed to date.

*Disease resistance.*—Neither resistance nor susceptibility to normal diseases and pests of *Sorbaria* observed to date.

*Temperature tolerance.*—USDA Zones 2 through 11.

*Drought tolerance.*—None observed.

What is claimed is:

1. A new and distinct cultivar of *Sorbaria* plant named 'COUSORB05' as herein illustrated and described.

* * * * *